United States Patent [19]

Bartels-Keith et al.

[11] 4,304,934
[45] Dec. 8, 1981

[54] SYNTHESIS OF AMINO HYDROXY CYCLOPENTENONES

[75] Inventors: James R. Bartels-Keith, Lexington; Eva R. Karger, Arlington; Jean B. Rogers, Concord, all of Mass.

[73] Assignee: Polaroid Corporation, Cambridge, Mass.

[21] Appl. No.: 221,523

[22] Filed: Dec. 30, 1980

[51] Int. Cl.$^3$ .................... C07C 85/00; C07C 85/11; C07C 85/24

[52] U.S. Cl. .................................. 564/1; 260/465.4; 556/443; 560/204; 562/526; 564/253; 564/300; 564/444; 564/448; 568/365

[58] Field of Search .................. 564/1, 448, 444, 253; 260/465.4; 562/526

[56] References Cited

U.S. PATENT DOCUMENTS 3,690,872  9/1972  Gabrielsen et al. ............. 96/66 HD

OTHER PUBLICATIONS

Kent et al., "Organic Synthesis", vol. 3, pp. 591–593 (1955).
Ruhlmann, "Synthesis", No. 5, pp. 236–253 (1971).
Schrapler et al., "Chem. Ber.", 97, pp. 1383–1389 (1964).
Blomquist et al., "Organic Synthesis", vol. 4, pp. 838–839 (1963).
Murakami et al., "Chem. Ab.", vol. 47, AB. No. 2714h (1953).
Batesky et al., "J. Org. Chem.", vol. 24, pp. 1694–1695 (1959).

Primary Examiner—John Doll
Attorney, Agent, or Firm—Sybil A. Campbell

[57] ABSTRACT

This invention relates to a method of synthesizing 3-amino-2-hydroxy-2-cyclopentenones possessing an aliphatic substituent in the 4-position which comprises reacting cyanoacetamide with an aliphatic aldehyde to yield the corresponding $\beta$-substituted-$\alpha,\alpha'$-dicyanoglutaramide, hydrolyzing the amide to the corresponding $\beta$-substituted glutaric acid, esterifying the acid to the corresponding dialkyl diester, converting the diester to a 1,2-bis(trimethylsiloxy)-4-substituted cyclopentene by reductive cyclization using chlorotrimethylsilane in the presence of sodium, hydrolyzing and oxidizing the bis(trimethylsiloxy) compound to the 2-hydroxy-4-substituted-2-cyclopentenone in the presence of a cupric salt, nitrosating the 2-cyclopentenone to the 2-hydroxy-4-substituted-5-oximino-2-cyclopentenone, converting the oxime to the 2-acetoxy-3-amino-4-substituted-2-cyclopentenone by reductive acetylation and removing the acetyl group by alkanolysis to yield the 3-amino-2-hydroxy-4-substituted-2-cyclopentenone product.

8 Claims, No Drawings

SYNTHESIS OF AMINO HYDROXY CYCLOPENTENONES

BACKGROUND OF THE INVENTION

1. Field of the Invention

This invention relates to a method of making 3-amino-2-hydroxy-2-cyclopentenones substituted in the 4-position with an alkyl group, particularly, a "bulky" alkyl group, e.g., a higher alkyl group containing more than 6 carbon atoms.

2. Description of the Prior Art

A variety of reductone compounds including amino reductones are known, and a number of such compounds have been used as reagents in photography. For example, U.S. Pat. No. 3,690,872 is directed to the use of certain amino hydroxy cycloalkenones as silver halide developing agents including 3-amino-2-hydroxy-2-cyclopentenones and 3-amino-2-hydroxy-2-cyclohexenones substituted in the 4-position with alkyl containing 1 to 5 carbon atoms. As discussed in this patent at column 3, lines 14–75, the preparation of 2-hydroxy-3-morpholino-2-cyclohexenone is typical of the method of preparing the amino hydroxy cycloalkenone developing agents and comprises refluxing equimolar amounts of morpholine, 3-chloro-1,2-cyclohexanedione and triethylamine in anhydrous ethyl acetate under an atmosphere of nitrogen.

Though it may be possible to synthesize 4-higher alkyl-3-chloro-2-hydroxy-2-cyclopentenone starting materials for the aforementioned substitution reaction, on the basis of our experience with a 4-undecyl-3-bromo compound it is believed that the substitution reaction would be unsuccessful. We have found that 3-bromo-2-hydroxy-4-n-undecyl-2-cyclopentenone is an exceptionally unreactive compound and that the bromine cannot be removed either by hydroysis or aminolysis without causing extensive decomposition. Indeed, with the bulky alkyl group, the conventional syntheses for these compounds are generally unsuitable.

The synthesis of α-methylglutaric acid by reacting cyanoacetamide and acetaldehyde to give α,α'-dicyano-β-methylglutaramide followed by hydrolyzing the amide with hydrochloric acid to give the product has been described by R. E. Kent and S. M. McElvain, Organic Synthesis, John Wiley & Sons, Vol. 3 (1955), pages 591–593. The reaction of carboxylic acids esters with sodium in inert solvents in the presence of trimethylchlorosilane has been reviewed by K. Rühlmann, Synthesis, 1971, pages 236–253 and as disclosed therein at pages 242–243, this reaction when applied to glutaric acid diethyl ester yields 1,2-bis-(trimethylsiloxy)-cyclopentene. See also, U. Schräpler and K. Rühlmann, Chem. Ber., 97, pages 1383–1389 (1964) for the reaction of trimethylchlorosilane with glutaric and other aliphatic dicarboxylic acid esters in the presence of sodium.

The use of cupric salts in the oxidation of ketols is known. For example, the oxidation of 2-hydroxycyclododecanone using cupric acetate/acetic acid to yield 1,2-cyclododecanedione has been reported by A. T. Blomquist and A. Goldstein, Organic Syntheses, John Wiley & Sons, Vol. 4 (1963), pages 838–839. The preparation of 1,2-cyclohexanedione monoxime by passing ethyl nitrite gas into a mixture of cyclohexanone and hydrochloric acid has been reported by M. Murakami and Y. Yukawa, Mem. Inst. Sci. Ind. Research Osaka Univ., 5, 150 (1947); Chem. Abstr., 47, 2714. Using isoamyl nitrite, D. C. Batesky and N. S. Moon, J. Org. Chem., 1959, 24, pages 1694–1695, have prepared the symmetrical dioximino ketones of cyclohexanone and its 4-methyl derivative.

SUMMARY OF THE INVENTION

According to the present invention, it has been found that 4-alkyl-3-amino-2-hydroxy-2-cyclopentenones and particularly 4-higher alkyl compounds of this type can be synthesized by utilizing the above-mentioned and other reactions, in a specific sequence, starting with a saturated aliphatic aldehyde, forming a β-alkyl-glutaric acid and its corresponding ester, cyclizing the ester to a 1,2-bis(trimethylsiloxy)-cyclopentene and oxidizing the cyclopentene under hydrolytic conditions to the 2-hydroxy-2-cyclopentenone followed by nitrosation, reductive acetylation and removal of the acetyl group to yield the 3-amino-2-hydroxy-4-alkyl-2-cyclopentenone product.

It is, therefore, the primary object of the present invention to provide a method of synthesizing 3-amino-2-hydroxy-2-cyclopentenones substituted in the 4-position with an alkyl group, particularly a higher alkyl group.

Other objects of this invention will in part be obvious and will in part appear hereinafter.

The invention accordingly comprises the processes involving the several steps and the relation and order of one or more of such steps with respect to each of the others which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

Specifically, the method of the present invention comprises:

(1) reacting 1 molar equivalent of an aldehyde having the formula RCHO wherein R is alkyl usually having 1 to 20 carbon atoms and at least 2 molar equivalents of cyanoacetamide in an inert polar solvent at room temperature in the presence of base to yield β-R-α, α'-dicyanoglutaramide;

(2) refluxing said β-R-α,α'-dicyanoglutaramide with concentrated hydrochloric acid in an inert organic solvent to yield β-R-glutaric acid;

(3) reacting said β-R-glutaric acid with at least the stoichiometric amount of an alkanol containing 1 to 4 carbon atoms at a temperature between about 0° C. and 120° C. in the presence of a mineral acid catalyst to yield the corresponding β-R-glutaric acid dialkyl ester;

(4) refluxing an admixture of 1 molar equivalent of said β-R-glutaric acid dialkyl ester and 4 molar equivalents of metallic sodium with 4 molar equivalents of trimethylchlorosilane in an inert hydrocarbon solvent having a boiling point greater than about 100° C. under anhydrous conditions to yield 1,2-bis(trimethylsiloxy)-4-R-cyclopentene;

(5) refluxing 1 molar equivalent of said 1,2-bis(trimethylsiloxy)-4-R-cyclopentene and 2 molar equivalents of a cupric salt in aqueous acetic acid solution to yield 4-R-2-hydroxy-2-cyclopentenone;

(6) reacting said 4-R-2-hydroxy-2-cyclopentenone and isoamylnitrite in equimolar amounts in an inert organic solvent at a temperature between about 0° C. and 25° C. in the presence of a mineral acid catalyst to yield 4-R-2-hydroxy-5-oximino-2-cyclopentenone;

(7) hydrogenating said 4-R-2-hydroxy-5-oximino-2-cyclopentenone in the presence of at least an equivalent amount of acetic acid, acetic anhydride or mixture of acetic acid and acetic anhydride at room temperature using a palladium-on-carbon catalyst to yield 2-acetoxy-3-amino-4-R-2-cyclopentenone; and (8) refluxing said 2-acetoxy-3-amino-4-R-2-cyclopentenone in a deareated, absolute alkanol containing 1 to 4 carbon atoms to yield 3-amino-2-hydroxy-4-R-2-cyclopentenone.

The above reaction sequence is illustrated below wherein R has the same meaning given above.

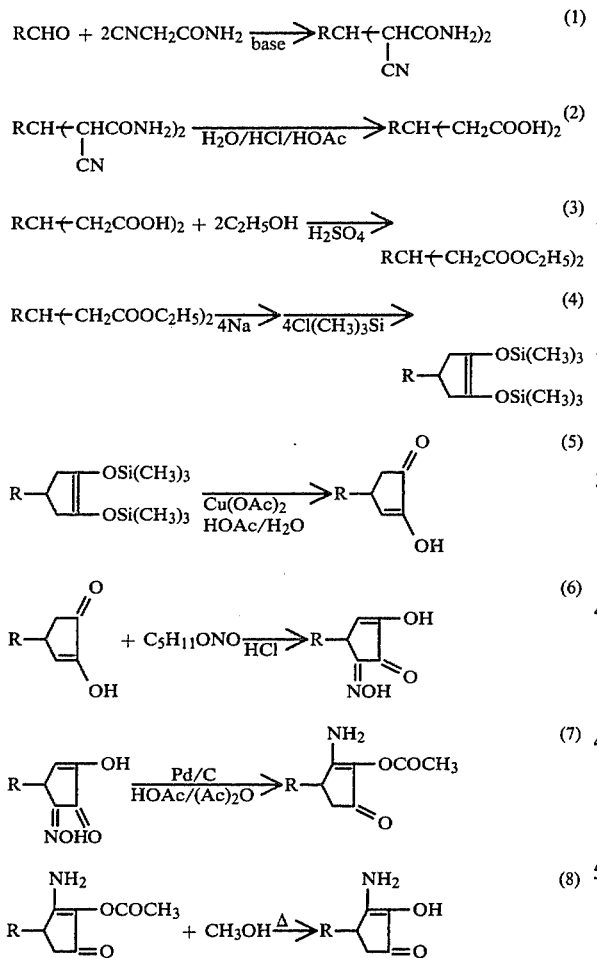

In carrying out the present invention, any aliphatic aldehyde may be employed as the starting material. Typical of the aldehydes that may be employed are those having the formula RCHO wherein R is alkyl having 1 to 20 carbon atoms which may be branched- or straight-chain alkyl.

Such aldehydes may be prepared by conventional methods including catalytic gas phase oxidation of alcohols using, e.g., spongy platinum as the catalyst; reduction of nitriles to aldimine salts which are then hydrolyzed to the aldehyde; and hydrogenolysis of acyl chlorides using a poisoned palladium catalyst on barium sulfate. It will be appreciated that many aldehydes, such as, phenylacetaldehyde, isovaleraldehyde, isobutyraldehyde, 2-methylundecanol and n-alkyl aldehydes having up to 12 carbon atoms are available commercially.

In step (1) of the subject method, the selected aldehyde is reacted with cyanoacetamide in an inert polar solvent in which the dicyanoglutaramide product crystallizes out. Water is useful as the solvent with the short-chain aldehydes, and alcohols, particularly, methanol is useful with the longer chain aldehydes. The reaction is most conveniently carried out at room temperature and is conducted in the presence of base, preferably, an organic base. Particularly useful organic bases are aliphatic amines, such as, triethylamine and piperidine. The cyanoacetamide should be used in an amount of at least 2 molar equivalents per molar equivalent of aldehyde. Ordinarily, 2 molar equivalents are employed, and an excess of up to about 0.20 molar equivalents may be used if desired.

The amide obtained in step (1) is converted to the corresponding β-substituted glutaric acid in step (2) by refluxing with concentrated hydrochloric acid in an inert organic solvent, such as, glacial acetic acid, and the glutaric acid obtained is then converted to the corresponding diester in step (3) by reaction with a lower alkanol having 1 to 4 carbon atoms, preferably, ethanol or methanol in the presence of a strong mineral acid. Concentrated sulfuric acid alone or in admixture with fuming sulfuric acid is conveniently employed as the mineral acid. The alkanol reactant may be used as the solvent in the esterification reaction, or the esterification may be carried out in a suitable inert organic solvent, for example, benzene or toluene. At least two molar equivalents of alkanol are used per molar equivalent of β-substituted glutaric acid, and where the alkanol is being employed as the reaction solvent, it is used in a large excess over stoichiometric amounts.

In step (4), the β-substituted glutaric acid diester and metallic sodium are admixed in an inert hydrocarbon solvent under anhydrous conditions employing 4 molar equivalents of sodium per molar equivalent of diester. The diester and sodium usually are stirred together at room temperature but higher temperatures may be employed. Ordinarily, the temperature ranges between about 25° and 125° C. Upon the addition of chlorotrimethylsilane, 4 molar equivalents per molar equivalent of diester, the reaction mixture is refluxed to yield the 1,2-bis(trimethylsiloxy)-4-substituted cyclopentene.

In step (5), any cupric salt may be employed for refluxing with the 1,2-bis(trimethylsiloxy) compound, for example, cupric chloride tetrahydrate or cupric acetate monohydrate. The salt is used in an amount of 2 molar equivalents per molar equivalent of 1,2-bis(trimethylsiloxy)-4-substituted-cyclopentene. The reaction preferably is carried out in glacial acetic acid solution, and in addition, an inert organic solvent may be employed, such as, methanol for ensuring complete solution of the reactants.

The 2-hydroxy-4-substituted-2-cyclopentenone obtained in step (5) is then reacted with an equimolar amount of isoamylnitrite in an inert organic solvent, e.g., 1,2-dimethoxyethane or chloroform in the presence of a mineral acid, such as, concentrated hydrochloric acid. The reaction temperature ordinarily ranges between about 0° and 25° C.

In the reductive acetylation of step (7), one molar equivalent of the 4-substituted-2-hydroxy-5-oximino-2-cyclopentenone obtained in step (6) is hydrogenated in the presence of 2 molar equivalents of acetic acid, acetic anhydride or preferably a mixture of acetic acid and acetic anhydride. The hydrogenation catalyst may be any of those commonly employed, for example, palladium-on-carbon, and hydrogen is introduced into the reaction solution at room temperature until no more hydrogen is taken up, usually about 2 molar equivalents of hydrogen per molar equivalent of the oximino cyclopentenone. Preferably, the reductive acetylation is carried out in the presence of a zinc salt, such as, zinc acetate to suppress reduction of the double bond of the cyclopentenone ring.

In step (8), the 2-acetoxy-3-amino-4-substituted-2-cyclopentenone is then refluxed in a deareated absolute alkanol having 1 to 4 carbon atoms to yield the 2-hydroxy-3-amino-4-substituted-2-cyclopentenone product. Preferably, methanol is employed since methylacetate is easier to remove from the reaction mixture than the higher alkylacetates because of its lower boiling point.

The following example is given to further illustrate the present invention and is not intended to limit the scope thereof.

EXAMPLE

Preparation of 3-amino-2-hydroxy-4-undecyl-2-cyclopentenone having the formula

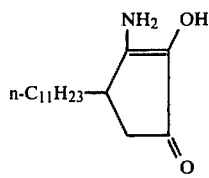

(1) Cyanoacetamide (4.2 g., 0.05 M) was suspended in 50 ml. of absolute methanol with stirring at room temperature. Dodecyl aldehyde (4.6 g., 0.025 M) was added followed by one ml. of piperidine. Precipitation of the reaction product began after a few minutes, and stirring of the reaction mixture was continued for 45 minutes. The mixture was filtered, and the solid was washed with 3 N hydrochloric acid, followed by water until neutral. The solid was then stirred with hot ethanol several times to a constant melting range of 168°–9° C. and then dried to yield 3.5 g. of β-undecyl-α,α'-dicyanoglutaramide.

The foregoing procedure was repeated using 1.0 M of the cyanoacetamide was 0.5 M of dodecyl aldehyde.

(2) β-Undecyl-α,α'-dicyanoglutaramide (17.7 g.) was stirred with 250 ml. of glacial acetic acid and heated to solution. 60 ml. of water and 120 ml. of conc. hydrochloric acid were added dropwise, and the solution was refluxed with stirring for 19 hours. After cooling, the reaction solution was poured into 3 liters of crushed ice, stirred and filtered to give a white solid. The solid was purified by taking up in ether, washing with water, drying and stripping. The residue was recrystallized from cyclohexane to give 10.8 g. of β-undecylglutaric acid (melting range 58°–9° C.).

(3) β-Undecylglutaric acid (10 g.) was dissolved in a mixture of 50 ml. conc. sulfuric acid and 50 ml. 15–18% fuming sulfuric acid. The clear solution was allowed to stand for 10 minutes and then was poured slowly into 500 ml. of ice cold absolute ethanol with stirring. The solution was concentrated to one-half volume on the roto evaporator and diluted with cold water. The resulting solution was extracted with ether, washed with saturated sodium chloride solution, 5% sodium bicarbonate solution and sodium chloride solution to neutral. After drying and stripping, a pale yellow oil was obtained which was purified by putting a benzene solution of the oil through Florisil (100 ml. benzene/150 ml. Florisil). Diethyl-β-undecyl glutarate, 11.8 g., was recovered as an analytically pure, colorless oil.

The above procedure was repeated by refluxing 165 g. of β-undecylglutaric acid with one liter of absolute ethanol, 500 ml. of dry benzene and 8 ml. of conc. sulfuric acid for 64 hours. After distillation under aspirator pressure to 600 ml., the mixture was diluted with cold sodium chloride solution and extracted as above to give 169 g. of yellow oil. After chromatography on Florisil (600 ml) in benzene, 163.5 g. of the diester was recovered as a pure colorless oil.

(4) Diethyl-β-undecyl glutarate (2.4 g., 0.007 M) was stirred under anhydrous conditions under nitrogen with metallic sodium (0.65 g.; 0.028 M) in 50 ml. of sodium dried xylene. The mixture was stirred at 120° C. for 2 hours using a Hershberg stirrer. At room temperature, with continued mixing, chlorotrimethylsilane (3.1 g.; 0.028 M) was added dropwise. The orange mixture decolorized. The reaction mixture was then heated to reflux and held there for one hour, cooled and filtered. The filtrate was stripped to give 2.4 g. of 1,2-bis(trimethylsiloxy)-4-undecyl cyclopentene as a yellow oil.

The foregoing procedure was repeated by stirring 100 g. of diethyl-β-undecyl glutarate, 2 liters of xylene and 27 g. of sodium under nitrogen at 115° C. for one hour; cooling to 87° C., adding dropwise 82.7 g. of chlorotrimethylsilane in 130 ml. xylene to maintain the temperature at 87°–90° C. (3–3½ hours); and refluxing for an additional one hour. The reaction mixture was then cooled and filtered, and the filtrate was distilled to give 107.5 g. of 1,2-bis(trimethylsiloxy)-4-undecyl cyclopentene as an oil.

(5) 40 g. of 1,2-bis(trimethylsiloxy)-4-undecyl cyclopentene, 40 g. of cupric acetate monohydrate, 10 ml. of water and 10 ml. of ethanol were stirred well and brought to reflux as rapidly as possible and refluxed for 30 minutes. The mixture was cooled quickly and filtered through Celite at room temperature. The resulting cake was washed thoroughly with acetic acid and ether. The filtrate was diluted with saturated sodium chloride solution and then extracted with fresh ether. The ether extracts were combined, washed with sodium chloride solution, cold 5% sodium bicarbonate solution and again with sodium chloride solution to neutral. The ether solution was then dried and stripped to leave 26 g. of yellow oil. The oil was mixed with 150 ml. of petroleum ether and refrigerated to give 9 g. of 2-hydroxy-4-undecyl-2-cyclopentenone as white plates (melting range 73°–4° C.).

(6) 2-Hydroxy-4-undecyl-2-cyclopentenone (1.1 g.; 0.0043 M) was dissolved in 10 ml. of 1,2-dimethoxyethane and 0.04 ml of conc. hydrochloric acid was added. The solution was cooled to 5° C. in an ice bath, and a solution of isoamylnitrite (0.5 g.; 0.0043 M) in 2 ml. of water was added dropwise. The reaction mixture was stirred for 2 hours at 5° C., then overnight at room temperature. Petroleum ether was added until a solid started to precipitate (about 80 ml.). The mixture was cooled in an ice bath, then filtered to yield 510 mg. of 2-hydroxy-5-oximino-4-undecyl-2-cyclopentenone as a yellow solid (melting range 144°–5° C.). Another 150 mg. of the oximino compound was obtained after allowing the filtrate to stand in the refrigerator overnight.

(7) 2-Hydroxy-5-oximino-4-undecyl-2-cyclopentenone (2.9 g.; 0.01 M), 80 ml. of acetic acid and 80 ml. of acetic anhydride were placed in a Parr bottle. After adding 280 mg. of 5% palladium-on-carbon, the reaction solution was placed on a hydrogenator, and hydrogen was introduced until no more was taken up. The reaction mixture took up approximately 0.02 M of hydrogen in about 30–60 minutes. The reaction mixture was then filtered to remove the palladium-on-carbon catalyst and the solvents were removed on a rotary evaporator at 45° C. The solid residue was washed well with anhydrous ethyl ether and dried to give 2.4 g. of 2-acetoxy-3-amino-4-undecyl-2-cyclopentenone as a white solid (melting range 134°–5° C.).

(8) To 25 ml. of well deareated absolute methanol was added 1.7 g. of 2-acetoxy-3-amino-4-undecyl-2-cyclopentenone, and the resulting mixture was heated to reflux. After about 10 minutes, the cyclopentenone was completely dissolved and after refluxing for another 2 hours, a solid started to precipitate. Refluxing was continued for 15 hours after which the methanol was removed by evaporation leaving 1.5 g. of pinkish solid. The solid was recrystallized from a warm solution of 90 ml. ethanol and 10 ml. water to give 1.2 g. of 3-amino-2-hydroxy-4-undecyl-2-cyclopentenone as shiny beige plates (melting range 212°–3° C. dec.) plus a second crop of 200 mg. (melting range 187°–201° C. dec.).

It will be appreciated that different aliphatic aldehydes, alkanols, mineral acid catalysts, hydrogenation catalysts and cupric salts may be substituted for those used in the foregoing example and that it is well within the skill of the art to select different inert solvents that are suitable for use in the various steps.

The aminoreductone compounds produced in accordance with the subject method find utility as reducing agents. For example, to illustrate the usefulness of 3-amino-2-hydroxy-4-undecyl-2-cyclopentenone as a reducing agent, a few crystals were dissolved in aqueous 1 N sodium hydroxide solution containing sufficient methanol to complete dissolution of the compound. A few drops of the solution were then placed on "Velox" paper (a photographic printing paper containing a silver chloride emulsion), and the silver chloride in the area of the applied solution was reduced as evidenced by the appearance of a dark spot. No darkening occurred with methanolic sodium hydroxide solution alone.

Since certain changes may be made in the above processes without departing from the scope of the invention herein involved, it is intended that all matter contained in the above description shall be interpreted as illustrative and not in a limiting sense.

What is claimed is:
1. A method which comprises
(1) reacting 1 molar equivalent of an aldehyde having the formula RCHO wherein R is alkyl and at least 2 molar equivalents of cyanoacetamide in an inert polar solvent at room temperature in the presence of base to yield $\beta$-R-$\alpha,\alpha'$-dicyanoglutaramide;
(2) refluxing said $\beta$-R-$\alpha,\alpha'$-dicyanoglutaramide with concentrated hydrochloric acid in an inert organic solvent to yield $\beta$-R-glutaric acid;
(3) reacting said $\beta$-R-glutaric acid with at least the stoichiometric amount of an alkanol containing 1 to 4 carbon atoms at a temperature between about 0° C. and 120° C. in the presence of a mineral acid catalyst to yield the corresponding $\beta$-R-glutaric acid dialkyl ester;
(4) refluxing an admixture of 1 molar equivalent of said $\beta$-R-glutaric acid dialkyl ester and 4 molar equivalents of metallic sodium with 4 molar equivalents of trimethylchlorosilane in an inert hydrocarbon solvent having a boiling point greater than about 100° C. under anhydrous conditions to yield 1,2-bis(trimethylsiloxy)-4-R-cyclopentene;
(5) refluxing 1 molar equivalent of said 1,2-bis(trimethylsiloxy)-4-R-cyclopentene and 2 molar equivalents of a cupric salt in aqueous acetic acid solution to yield 4-R-2-hydroxy-2-cyclopentenone;
(6) reacting said 4-R-2-hydroxy-2-cyclopentenone and isoamylnitrite in equimolar amounts in an inert organic solvent at a temperature between about 0° C. and 25° C. in the presence of a mineral acid catalyst to yield 4-R-2-hydroxy-5-oximino-2-cyclopentenone;
(7) hydrogenating said 4-R-2-hydroxy-5-oximino-2-cyclopentenone in the presence of at least an equivalent amount of acetic acid, acetic anhydride or mixture of acetic acid and acetic anhydride at room temperature using a palladium-on-carbon catalyst to yield 2-acetoxy-3-amino-4-R-2-cyclopentenone; and
(8) refluxing said 2-acetoxy-3-amino-4-R-2-cyclopentenone in a deareated, absolute alkanol containing 1 to 4 carbon atoms to yield 3-amino-2-hydroxy-4-R-2-cyclopentenone.

2. A method as defined in claim 1 wherein R is alkyl containing 1 to 20 carbon atoms.

3. A method as defined in claim 2 wherein said R is n-undecyl.

4. A method as defined in claim 3 wherein said alkanol in said step (3) is ethanol.

5. A method as defined in claim 4 wherein said mineral acid catalyst in said step (3) is concentrated sulfuric acid.

6. A method as defined in claim 5 wherein said cupric salt in said step (5) is cupric acetate monohydrate.

7. A method as defined in claim 6 wherein said mineral acid catalyst in said step (6) is concentrated hydrochloric acid.

8. A method as defined in claim 7 wherein said alkanol in said step (8) is methanol.

* * * * *